United States Patent [19]
Gast

[11] 3,977,786
[45] Aug. 31, 1976

[54] MODULAR OPTICAL SPECTROMETER SYSTEM

[75] Inventor: Jürgen Gast, Forchheim, Germany

[73] Assignee: Bruker-Physik AG, Karlsruhe, Forchheim, Germany

[22] Filed: Apr. 25, 1974

[21] Appl. No.: 463,975

[30] Foreign Application Priority Data
Apr. 26, 1973    Germany.......................... 2321097

[52] U.S. Cl................................. 356/88; 356/93; 356/96; 356/97; 356/244; 356/106 S
[51] Int. Cl.²..................... G01J 3/42; G01N 21/16
[58] Field of Search .............. 356/246, 244, 74, 88, 356/93, 95, 96, 97, 101, 106 IS, 205, 206

[56] References Cited
UNITED STATES PATENTS

| | | | |
|---|---|---|---|
| 2,404,064 | 7/1946 | Heigl et al. ............................ | 356/96 |
| 2,715,851 | 8/1955 | Derr...................................... | 356/96 |
| 3,045,534 | 7/1962 | Adams................................... | 356/88 |
| 3,286,582 | 11/1966 | Mertz ............................. | 356/106 IS |
| 3,554,648 | 1/1971 | Boostrom et al. ..................... | 356/96 |
| 3,737,234 | 6/1973 | Shibata et al. ......................... | 356/88 |

OTHER PUBLICATIONS

Jarrel–Ash Bulletin No. 12; received Dec. 5, 1968.

*Primary Examiner*—Vincent P. McGraw
*Attorney, Agent, or Firm*—Pennie & Edmonds

[57] ABSTRACT

A modular system for performing optical spectroscopy measurements comprising enclosed modules with ports through which optical beams may pass into and out of the modules. The modules may be joined together with the ports aligned and are interchangeable in the sense that the focal point of the optical beam directed out of any output port has the same location relative to the output port.

10 Claims, 1 Drawing Figure

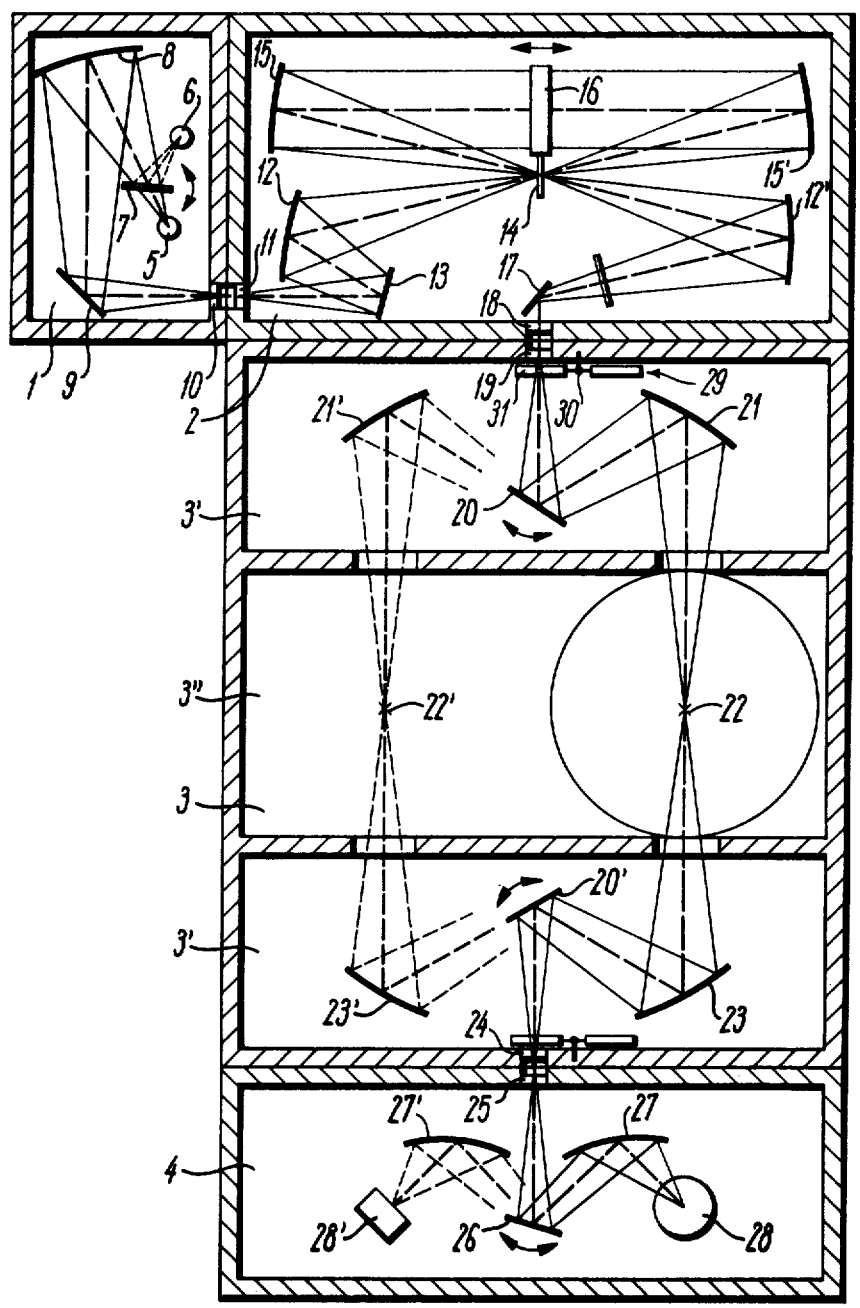

MODULAR OPTICAL SPECTROMETER SYSTEM

BACKGROUND OF THE INVENTION

This invention relates to a modular optical system for making spectroscopic measurements. The particular embodiment of the invention disclosed is an infrared Fourier-transform spectrometer system which can maintain the infrared beam in a vacuum.

A book entitled *Introductory Fourier Transform Spectroscopy* by Robert John Bell (Academic Press 1972) contains a chapter describing commercially available optical Fourier-transform spectrometers. The spectrometers described in this chapter are limited in that they were all designed and constructed for a few particular modes of operation. Thus an experimenter who wished to rearrange the elements making up one of these spectrometers into a configuration more suitable for his requirements was faced with the difficult task of redesigning the optics of the spectrometer. An experimenter might wish to investigate the spectral characteristics of a particular beam source and for this purpose a sample chamber is not needed. However it is impossible to remove the sample chamber from one of the prior-art spectrometers and connect the detector unit in its place without redesigning the optics of the spectrometer.

SUMMARY OF THE INVENTION

To avoid such problems the present invention contemplates assembling an optical spectrometer out of a collection of enclosed modules. The modules have ports in their enclosures for admitting or projecting the optical beams used in the spectrometer. As used herein, the term "optical beam" refers to a beam of electromagnetic radiation whose frequency spectrum lies in the infrared, visible and ultraviolet ranges. The modules are constructed so that they may be readily connected together with their ports aligned. Thus any module with an output port may be rigidly joined to any module having an input port in such a way that an optical beam directed out of the output port of the first module will pass into the input port of the second. The individual modules of the invention contain optical elements which permit them to perform the functions of the components of a standard optical spectrometer. Thus a Fourier-transform spectrometer might be assembled from a source module, an interferometer module, a sample-chamber module, and a detector module.

The invention further contemplates making the modules so that they may be joined together in a variety of sequences and combinations. To accomplish this, the optical elements in the modules are so designed that the focal point of the optical beam directed out of the output port of any module has the same location relative to the output port. Furthermore the optical elements associated with the input ports are designed to accept and process a beam whose focal point is located at this position. Thus any module having an output port may be readily joined to any module having an input port without the need to make any substantial changes in the optics of either module. The output beams may be further standardized to advantage by making each beam have the same aperture angle as well as having the same focal-point location.

In a preferred embodiment of the invention the focal point of each beam projected out of an output port of a module is located in a plane situated between the output port and the input port of another module which is joined to the first module. This arrangement is advantageous because by focusing the beam on a point between two modules, the beam has a small diameter as it passes between the modules. The input and output ports and any windows associated with them can therefore have a small diameter. Small diameter windows are easier to seal than larger windows and may be considerably less expensive if they must be made from single crystals, as is required for the optics of spectrometers covering certain frequency ranges.

The direction of propagation of the beam projected from an output port may be selected at will so long as the selected direction is used for all of the modules. In preferred embodiments of the invention the direction of propagation is specified to make an angle of 0°, 30°, or 45° with the normal to the plane situated between two modules which are joined together. Polarization of the beam by the windows is ordinarily minimized when this angle is chosen to be 0°.

The enclosures of the modules may be sealed and made air-tight if it is desired either to maintain the optical beam in a vacuum or in a particular atmosphere. As pointed out above, sealing the windows is facilitated by locating the focal points of the beams between the joined-together modules. Since the modules may thus be sealed individually, the invention does not lose its great flexibility even when operated as a vacuum spectrometer.

BRIEF DESCRIPTION OF THE DRAWING

These and other objects, features, and elements of the invention will become more readily apparent from the following detailed description of the drawing. The drawing depicts the invention embodied in an infrared Fourier-transform spectrometer system. The system comprises four modules, numbered 1 through 4 in the drawing. The electronic and recording elements of the spectrometer system are not necessary to appreciate the invention and are not shown.

DETAILED DESCRIPTION OF THE DRAWINGS

The spectrometer system in the drawing comprises four modules: module 1 containing a source of an optical beam, module 2 containing an interferometer, module 3 containing holders for a sample and a reference sample, and module 4 containing an optical detector.

Module 1 is provided with two sources of infrared radiation: source 5 and source 6. These two sources produce radiation of different spectral characteristics. In order to select one or the other, a plane folding mirror 7 is brought into one of two positions in which it either allows the radiation from source 5 to fall onto spherical mirror 8 or reflects the radiation from source 6 onto spherical mirror 8. Spherical mirror 8 reflects the beam originating from the selected source onto a stationary plane mirror 9, which in turn reflects the beam out through the windowed output port 10 in module 1. Spherical mirror 8 is shaped and positioned so that its focal point is located in the plane of the outer surface of module 1 or just outside of this plane.

A windowed input port 11 is located in module 2 just opposite port 10 of module 1. Module 2 contains an ellipsoidal mirror 12 whose focal point coincides with the focal point of spherical mirror 8. In order to locate ellipsoidal mirror 12 near the wall of module 2, a plane deflecting mirror 13 is provided in module 2. The second focal point of ellipsoidal mirror 12 is located on beam splitter 14. Thus the infrared beam from spherical mirror 8 is focused by ellipsoidal mirror 12 onto beam-splitter 14. Beam splitter 14 is an amplitude-dividing beam splitter of the type commonly used in infrared interferometers. Beam splitter 14 is located at the focal point of an extra-axial parabolic mirror 15. The beam splitter 14 reflects half of the infrared beam to parabolic mirror 15, which forms the beam into a parallel beam and sends it a reflecting surface of double plane mirror 16. The double plane mirror 16 may be moved by measurable amounts in the direction parallel to the direction of propagation of the beam falling upon it in order to vary the phase characteristic of the beam reflected by the beam splitter 14 relative to the portion of the beam which passes through the beam splitter.

The portion of the beam allowed to pass by the beam splitter 14 strikes an extra-axial parabolic mirror 15', which is positioned symmetrically with respect to parabolic mirror 15, the plane of symmetry being defined by the plane of beam splitter 14. Similarly, an ellipsoidal mirror 12' is provided symmetrically to ellipsoidal mirror 12. The interferometer of module 2 is thus constructed in the manner of a mirror image. The rays reflected by the two plane mirror surfaces of the double plane mirror 16 are partly transmitted by beam splitter 14 and partly reflected. The two portions are guided by way of ellipsoidal mirror 12' to a stationary plane deflecting mirror 17, which reflects the beam out of the chamber 2 through a windowed output port 18. The beam is focused to a point located in or slightly outside the surface plane of the adjacent wall of the module 2.

Provided adjacent to port 18 of module 2 is windowed input port 19 of module 3. Module 3 is divided into two outer chambers 3' and an inner chamber 3'', which together form the interior of module 3. The two outer chambers 3' are constructed in an identical manner. Each comprises a plane folding mirror 20 (20') which may be moved into two positions by a common actuating mechanism which is not shown. Symmetrical, extra-axial ellipsoidal mirrors 21, (23) and 21', (23') are provided. In one position of the folding mirror 20, the beam entering through the window 19 is directed to ellipsoidal mirror 21, in the other position, to ellipsoidal mirror 21'. The beam which is reflected by the two ellipsoidal mirrors 21, 21', is focused either at point 22 or point 22', depending on the position of mirror 20. The point 22 is the place at which the sample through the infrared beam is to be passed is held. A reference sample, through which the beam may also be passed, is held at point 22'. Chamber 3'' is thus the actual sample chamber. The beam passed through the sample or reference sample strikes against symmetrical ellipsoidal mirrors 23, 23', which reflect the beam outwards by way of the folding mirror 20', through a windowed output port 24. The shape and arrangement of the ellipsoidal mirrors 21, 21' and 23, 23' are such that the incoming beam focuses either at point 22 or 22' and the beams leaving either of these points focus at a point which is located in or somewhat outside the surface plane of the wall of the module 3 in which the port 24 is located.

Adjoining the chamber 3', from which the beam is projected, is module 4, into which the beam passes through a windowed input port 25. The beam thus strikes a movable plane mirror 26 which, depending upon its position, directs the beam by way of an ellipsoidal mirror 27 to an infrared detector 28, or by way of ellipsoidal mirror 27' to another infrared detector 28'. The two infrared detectors 28, 28' and the two ellipsoidal mirrors 27, 27' are arranged symmetrically with respect to the axis of the incoming beam. The actuation of the folding mirror 26 may be coupled with the actuation of the folding mirror 7, in order to guide the beam of the infrared source 5 to the detector 28 and the beam of the infrared source 6 to the detector 28'. Filter wheels 29 with variable filters 31 may be provided at the ports, making it possible to bring the various filters 31 in the beam path by rotating a shaft 30.

If it is desired to maintain the optical beam of the spectrometer substantially in a vacuum, the ports in the modules may be covered with suitable transparent windows sealed to the enclosure and each module may be individually evacuated. A second way of evacuating the system may also be used. The modules making up the system may be sealed together and the entire system evacuated as a unit. In this way the ports may be left uncovered, which may be advantageous if suitable material for windows is difficult to find.

As will be obvious to those skilled in the art, numerous modifications may be made to the preferred embodiment described and illustrated herein without departing from the invention as defined in the claims. For example, modules performing other functions useful for optical spectroscopy measurements may be used in addition to or instead of the modules described above. The invention contemplates using sources and detectors in the visible and ultraviolet frequency ranges as well as the infrared range. Different sample chamber configurations may be used. For example, a sample-chamber module may have more than two ports and other provisions for irradiating the sample with a second beam of optical radiation. Modules containing conventional monochrometers as well as interferometers of different types may also be used.

I claim:

1. An optical spectrometer system comprising:
    a first enclosed module having a source of a beam of optical radiation and an output port through which the optical beam can pass;
    a second enclosed module having a detector of optical radiation and an input port through which the optical beam can pass;
    a third enclosed module having an input port and an output port through which the optical beam can pass and means for holding a sample in the path of the optical beam;
    means for rigidly joining the modules together with each of the output ports in optical alignment with an input port; and
    means associated with each module having an output port for focussing the optical beam passing through the output port to a point, each such focal point being located at substantially the same position with respect to its output port.

2. A system according to claim 1 in which the focal point of the optical beam directed out of the output port of any module is located in a plane situated between the output port of said module and an input port of another module to which it is joined.

3. A system according to claim 1 further comprising means for providing that the optical beam directed out of the output port of any module has the same aperture angle.

4. A system according to claim 1 further comprising means for providing that the direction of propagation of the optical beam directed out of the output port of any module forms a 45° angle with the normal to a plane which is situated between the output port of said module and an input port of another module to which it is joined.

5. A system according to claim 1 further comprising means for providing that the direction of propagation of the optical beam directed out of the output port of any module forms a 30° angle with the normal to a plane which is situated between the output port of said module and an input port of another module to which it is joined.

6. A system according to claim 1 further comprising means for providing that the direction of propagation of the optical beam directed out of the output port of any module forms a 0° angle with the normal to a plane which is situated between the output port of said module and an input port of another module to which it is joined.

7. A system according to claim 1 in which the third module contains an interferometer comprising:
an amplitude-dividing beam splitter;
a movable mirror;
means for directing an optical beam onto said mirror; and
means for moving said mirror in the direction of propagation of said beam.

8. A system according to claim 1 in which at least one of the enclosed modules has an air-tight enclosure.

9. A system according to claim 1 further comprising a fourth module containing an interferometer comprising:
an input port and an output port through which the optical beam can pass;
an amplitude-dividing beam splitter;
a movable mirror;
means for directing an optical beam onto said mirror; and
means for moving said mirror in the direction of propagation of said beam.

10. A system according to claim 1 further comprising:
means for providing that the focal point of the optical beam directed out of the output port of any module is located in a plane situated between the output port of said module and an input port of another module to which it is joined;
means for providing that the optical beam directed out of the output port of any module has the same aperture angle;
means for holding a reference sample in the third module; and
means for directing the optical beam along one of two paths through the third module, one path passing through the sample held in the module and the other path passing through the reference sample held in the module.

* * * * *